United States Patent
White (10) Patent No.: US 9,581,538 B2
(45) Date of Patent: Feb. 28, 2017

(54) METHOD AND APPARATUS FOR ASSESSMENT OF ADHESION OF LABELS

(71) Applicant: PepsiCo, Inc., Purchase, NY (US)

(72) Inventor: Charles White, Parsippany, NJ (US)

(73) Assignee: PepsiCo, Inc., Purchase, NY (US)

( * ) Notice: Subject to any disclaimer, the term of this patent is extended or adjusted under 35 U.S.C. 154(b) by 327 days.

(21) Appl. No.: 14/206,349

(22) Filed: Mar. 12, 2014

(65) Prior Publication Data

US 2015/0260635 A1    Sep. 17, 2015

(51) Int. Cl.
*G01N 19/04*    (2006.01)
*G01N 3/00*     (2006.01)

(52) U.S. Cl.
CPC .............. *G01N 19/04* (2013.01); *G01N 3/00* (2013.01)

(58) Field of Classification Search
CPC .................................. G01N 19/04; G01N 3/00
See application file for complete search history.

(56) References Cited

U.S. PATENT DOCUMENTS

| | | | | |
|---|---|---|---|---|
| 5,435,879 A * | 7/1995 | Knutson | ................ | C09J 7/0217 156/327 |
| 5,878,901 A * | 3/1999 | Grosskopf | .............. | B32B 27/08 215/399 |
| 2004/0126520 A1* | 7/2004 | Samarcq | ............. | B29C 49/0005 428/35.7 |
| 2008/0063835 A1* | 3/2008 | Iwasa | ...................... | B32B 27/08 428/137 |
| 2013/0292031 A1* | 11/2013 | Cooper | ................... | B32B 27/32 156/60 |

* cited by examiner

*Primary Examiner* — Hezron E Williams
*Assistant Examiner* — David Z Huang
(74) *Attorney, Agent, or Firm* — Sterne, Kessler, Goldstein & Fox P.L.L.C.

(57) ABSTRACT

An apparatus and method for assessing adhesion of labels applied to a bottle. A label adhered to the outer surface of the bottle is split vertically to form a leading end and trailing end of the label. The bottle may be secured to a support structure and the trailing end of the bottle may be secured to a weighted structure. The bottle is suspended in a heated chamber via the support structure until the adhesive fails, causing the weighted clamp to fall within the chamber. An elapsed time to failure is determined for the bottle and compared to a benchmark time and/or metric as an indicator of how the adhesive is likely to perform during shipping and/or storing the bottle.

20 Claims, 7 Drawing Sheets

| Failure Time (minutes) | Rating |
|---|---|
| 5:01 and above | 0 |
| 3:01 – 5:00 | 1 |
| 2:01 – 3:00 | 2 |
| 1:31 – 2:00 | 3 |
| 1:01 – 1:30 | 4 |
| 1:00 and below | 5 |

METHOD AND APPARATUS FOR ASSESSMENT OF ADHESION OF LABELS

BACKGROUND

The strength of adhesion between a label and an outside surface of a bottle is of considerable interest to adhesive manufacturers, bottling plants, marketers, compliance officers, and the like. For example, weak adhesion between the label and the outside surface of the bottle may lead to the label working loose (and in some cases even separating from the bottle completely) during shipping or storing the bottle. Such a weak bond may thus lead to a product that is not attractive to consumers (e.g., a bottle with a loose label) or a product that does not conform to labeling requirements (e.g., Food and Drug Administration (FDA) regulations).

In some instances, transporting and/or storing a labeled bottle may present conditions that expedite adhesive failure. For example, labeled bottles are often subjected to elevated temperatures and/or high humidity during transportation and storage prior to being delivered to retailers. In addition to decreasing the effectiveness of the adhesive, this elevated temperature and/or humidity may cause the bottle and its contents to expand and place increased stresses on the bond, further accelerating adhesive failure. Accordingly, bottling plants, manufacturers, etc., test adhesives used in bottling applications to ensure that the bond will withstand the anticipated conditions during shipping, storage, and the like.

Traditionally, this testing is performed using expensive machinery located at a remote laboratory. At these laboratories, dynamic testing equipment (e.g., an environmental chamber or the like) is used to quantify the strength of an adhesive used during a particular bottling batch. For example, a bottling plant may collect one or more adhesive samples from a particular batch and send them to a laboratory for testing. The laboratory may then subject the one or more samples to a test using equipment which determines how much time is required to cause failure of the adhesive. Generally, the more time required to cause failure indicates a stronger adhesive bond. The results of the test are then returned to the bottling plant or the like, which may then proceed accordingly. For example, if the adhesive performs in an acceptable range, the bottling plant may ship the bottles. Alternatively, if the adhesive does not perform in an acceptable range, the bottling plant may destroy or re-label the bottles (if the bottles have not already shipped).

This testing scheme suffers many drawbacks. For example, the machinery used to test the samples may be expensive and/or require trained personnel to operate in order to obtain accurate results. Accordingly, such equipment may be located offsite causing a significant delay between the time a sample is sent for testing and the time the results are returned. For example, two weeks is a typical turnaround to receive results of an offsite test. In the meantime, the bottling plant may have labeled thousands of bottles which may ultimately be unusable (should the tests indicate the adhesive is ineffective). Further, this traditional testing typically involves only labels and glue (and not the bottle). Thus, these tests cannot predict the effects of "real-world" conditions on the adhesive. For example, these tests are unable to measure the effects of long-term creep on the adhesive caused by an expanding bottle stored at high temperatures.

Accordingly, there remains a need to provide a method and/or apparatus to test the adhesion of a label to an outside surface of a bottle that overcomes one or more of the above deficiencies.

BRIEF SUMMARY

One or more objects of the disclosure address the above shortcomings of traditional adhesive testing apparatuses and methods.

According to a first embodiment of the disclosure, a method is provided for assessing the adhesion of a label to an outer surface of a bottle. The method comprises filling the bottle with warm liquid, slitting the label adhered to the outside surface of the bottle to form a leading end and a trailing end of the label at the slit, attaching the leading end of the label or the bottle itself to a support structure, suspending the bottle in a heated chamber via a support structure such that the bottle hangs below the support structure, and determining an elapsed time before the label disengages from the bottle. In some embodiments, a weight may be fixed to the trailing end of the label such that, when the bottle is suspended in the heated chamber, the weight hangs below the bottle. Such a method may be easier, cheaper, and/or quicker than currently used methods while simulating "real world" shipping and/or storing conditions.

According to another aspect of the disclosure, a method is provided for assessing the adhesion of labels to the outside surfaces of a plurality of bottles, such as a plurality of bottles from a common labeling batch. The method comprises filling the plurality of bottles with warm liquid, storing each bottle in an oven, slitting the label adhered to the outside surface of each bottle to form a leading end and a trailing end of the label at the slit when removed from the oven, attaching the leading end of each label or each bottle itself to a support structure, suspending each bottle in a heated chamber via the support structure such that the bottle hangs below the support structure, determining an elapsed time before the label disengages from each bottle, and averaging the elapsed time for each bottle to form an average elapsed time for the plurality of bottles. In some embodiments, a weight may be fixed to the trailing end of the label of each bottle such that, when the bottle is suspended in the heated chamber, the weight hangs below the bottle.

According to other aspects, an apparatus is provided for assessing the adhesion of a label to an outside surface of a bottle. The apparatus may comprise a weighted clamp configured to attach to a trailing end of the label adhered to the outside surface of the bottle, a support structure configured to attach to a leading end of the label or the bottle itself, and a heated chamber configured to receive the weighted clamp and the support structure in a testing position, wherein, when in the testing position, the weighted clamp hangs below the support structure.

BRIEF DESCRIPTION OF THE DRAWINGS

The above and other features, aspects, and advantages of the invention will be fully apparent and understood from the following detailed description, taken together with the appended drawings, wherein.

DETAILED DESCRIPTION

Figure 1:
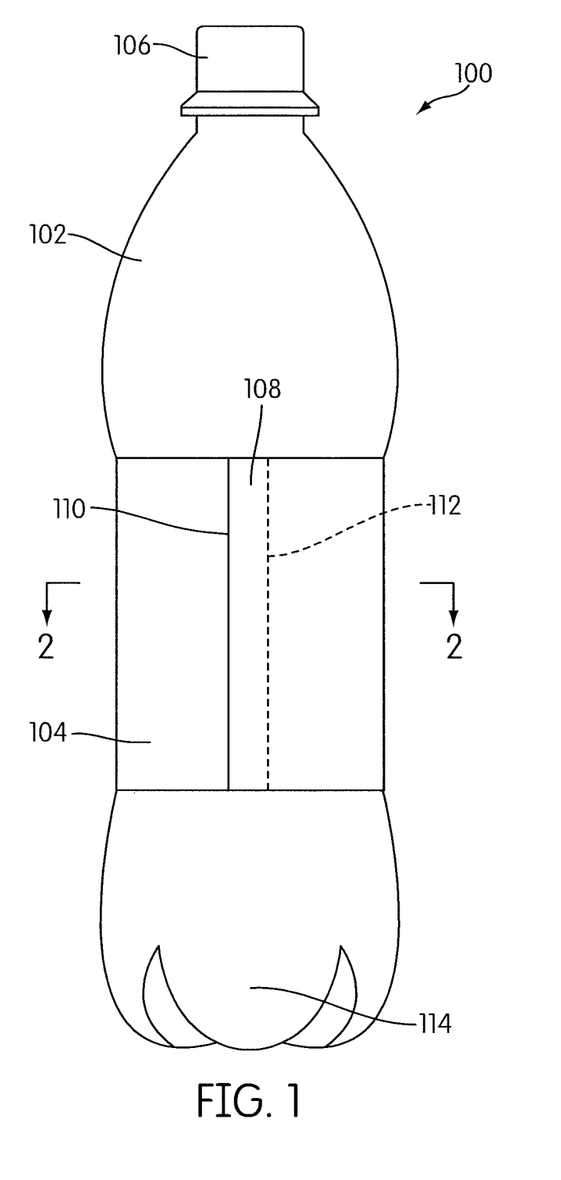
FIG. 1 is a front view of a bottle with a label adhered to an outside surface to be tested according to at least one embodiment of the disclosure.

FIG. 1 illustrates a bottle 100 which may be used in connection with one or more embodiments of the disclosure. The bottle 100 comprises a generally elongated plastic outer surface 102 comprising a cap 106 removably attachable to a top portion of the bottle 100 to enclose, e.g., a consumable liquid contained therein, and a base structure 114 configured to, e.g., support the bottle 100 in an upright position when placed on a support surface. The bottle 100 may be constructed of any well-known material in the art, and, in some embodiments, the bottle 100 may be made of polyethylene terephthalate ("PET"). The bottle 100 further comprises a label 104 adhered to the outer surface 102. In some embodiments, the label 104 may be generally rectangular in shape and wrapped around the outer surface 102 of the bottle 100. The label 104 may comprise a seal 108 where a first portion of the label 104 overlaps and is adhered to a second portion of label 104.

Figure 2:
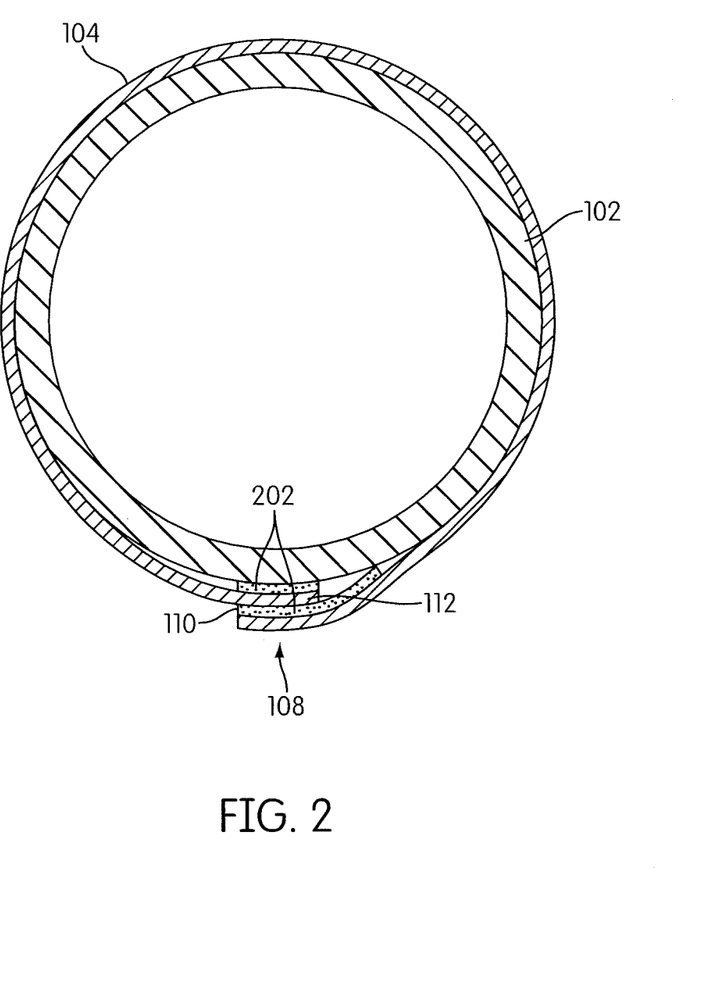
FIG. 2 is a cross-sectional view along line 2-2 of the bottle depicted in FIG. 1.

For example, and as may be more apparent with reference to FIG. 2, the label 104 may comprise a first edge 110 which overlaps a second edge 112. The portions of the label 104 which overlap may be adhered to each other using any desirable adhesive 202. Further, the adhesive 202 may be used to adhere portions of the label 104 to the outer surface 102 of the bottle 100. Thus, the label 104 may be adhered to itself or the bottle 100 at one or more locations around the circumference of the bottle 100. As depicted in FIG. 2, the adhesive 202 is applied both between the label 104 and the outer surface 102 of bottle 100 and between two portions of the label 104 at a seal 108.

Figure 4:
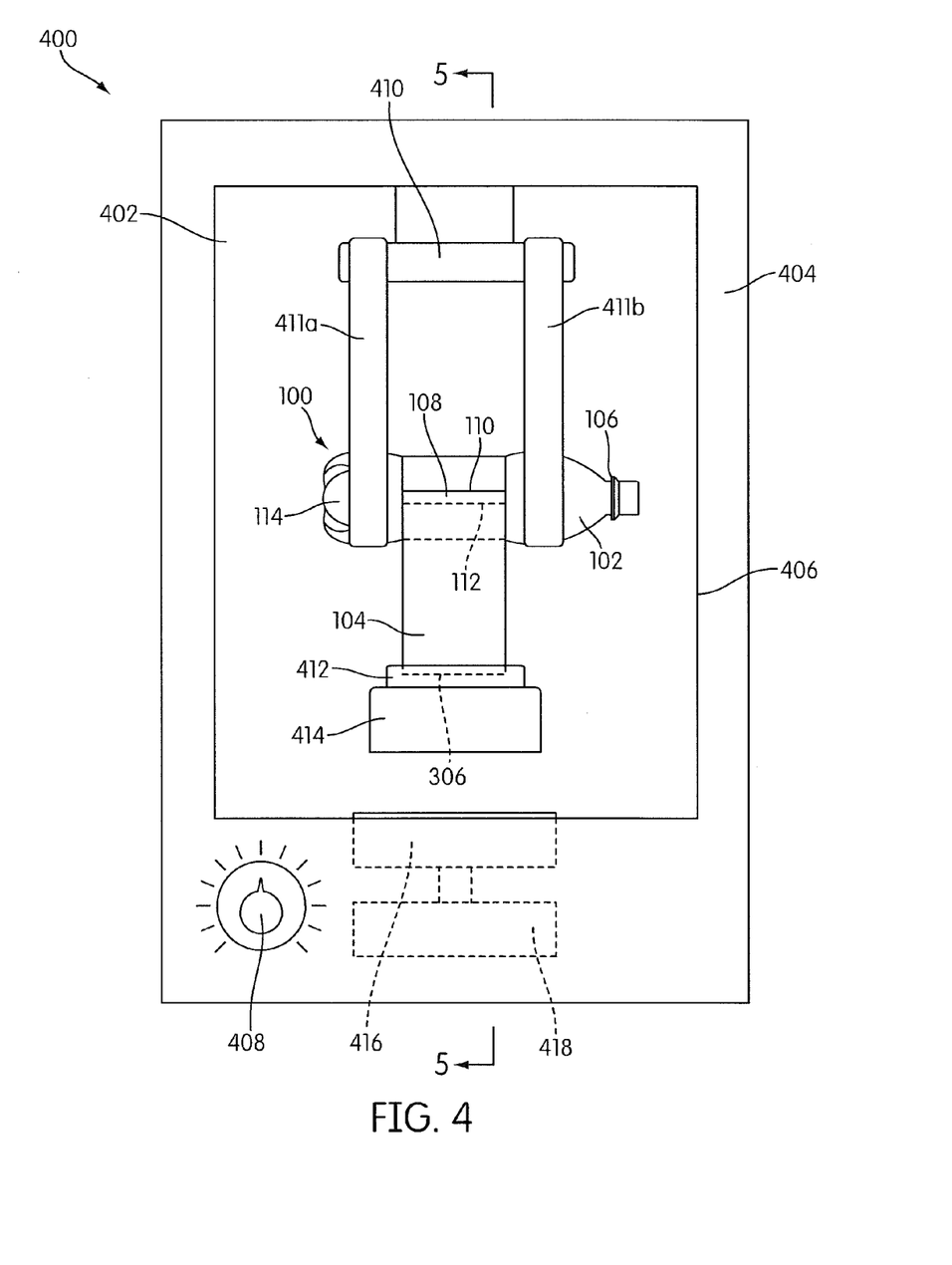
FIG. 4 is a front view of a label tester used to assess the adhesion of the label to the bottle depicted in FIG. 1.
Figure 5:
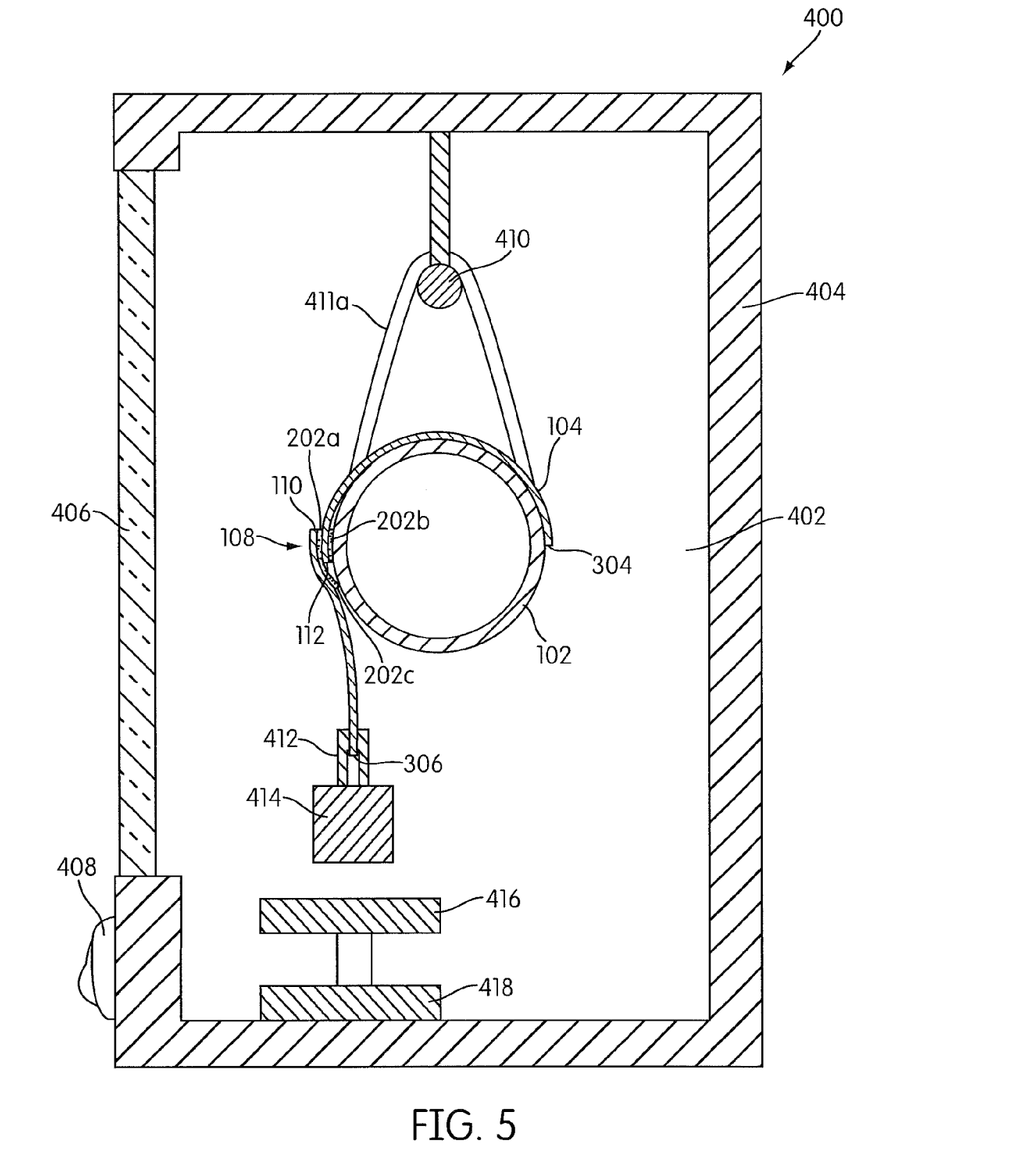
FIG. 5 is a cross-sectional view along line 5-5 of the label tester depicted in FIG. 4.

According to some aspects of the disclosure, a user may wish to assess the strength of the bond of the adhesive 202 in order to, e.g., predict the performance of the adhesive 202 during transporting and/or storing the bottle 100. Thus, according to some embodiments, a static load label tester 400 (which will be discussed more fully) may be used to asses, e.g., the adhesion of the label 104 to the outer surface 102 of the bottle 100. As depicted in FIGS. 4 and 5, in some embodiments the static load label tester 400 may comprise a body 404 enclosing a heated chamber 402, a transparent door 406, an instrument panel 408, a support structure 410, and a weighted clamp 412. The heated chamber 402 may be a temperature-controlled chamber (adjustable using, e.g., an instrument panel 408) in which a desired internal temperature may be maintained. For example, in some embodiments the heated chamber 402 may be configured to maintain an internal temperature of, e.g., approximately 100 degrees Fahrenheit.

Figures 3A, 3B, 3C:
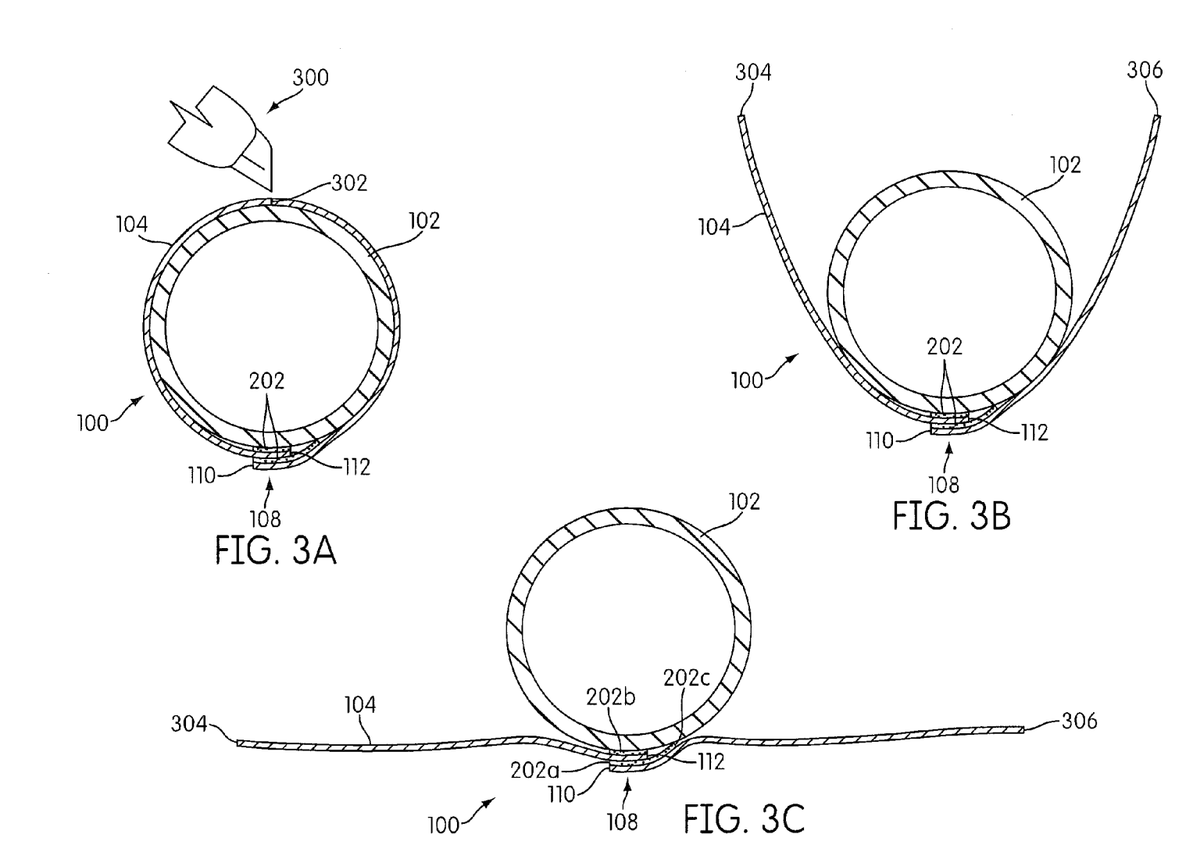
FIGS. 3A-3C are cross-sectional views along line 2-2 of the bottle depicted in FIG. 1 illustrating a slit in the label according to some aspects of the disclosure.

According to some aspects of the disclosure, a user of the static load label tester 400 may prepare the label 104 before it is placed in the static load label tester 400 as depicted in FIGS. 3A-3C. For example, in some embodiments one or more clamps used in connection with the static load label tester 400 may be configured to attach to one or more free ends of the label 104. In such embodiments, a user may slit the label 104 to form the free ends of the label 104. FIGS. 3A-3C schematically illustrate prepping the label 104 to be used in the static load label tester 400 according to one embodiment of the disclosure. As shown in FIG. 3A, in some embodiments the label 104 may first be separated at a slit 302 using, e.g., a cutting tool 300. The label 104 may be slit in a top to bottom direction; i.e., the label 104 may be split in a direction generally parallel to the first edge 110 or the second edge 112 and generally perpendicular to the cross-section of the bottle 100 depicted in FIG. 3A. In some embodiments, the slit 302 may be located, e.g., approximately 180 degrees around the circumference of the cross-section of the bottle 100 from the seal 108.

As can be more readily seen in, e.g., FIGS. 3B and 3C, the slit 302 in the label 104 forms two free ends. For example, when the label 104 is separated along its entire length from top to bottom along the slit 302, a leading end 304 and a trailing end 306 are formed as free ends. Thus, a user may peel the ends 304 and 306 away from the outer surface 102 of the bottle 100 as depicted in FIG. 3B. For some applications of the adhesive 202 on the bottle 100, the adhesive 202 may be applied around the circumference of the bottle 100 at multiple locations. For example, in some embodiments the adhesive 202 may be generally applied between the label 104 and the outer surface 102 of the bottle 100 around the entire circumference of the bottle 100, and thus in order to peel the free ends 304 and 306 away from the outer surface 102 of the bottle 100, a user may be required to remove portions of the adhesive 202. For example, if the adhesive 202 were applied at or near the slit 302, a user may need to peel the label 104 away from the adhesive 202 (e.g., apply enough force to counteract the bonding force of the adhesive 202) in order to form the leading end 304 and the trailing end 306.

However, in other embodiments, the adhesive 202 may not be applied between the outer surface 102 of the bottle 100 and the label 104 at or near the location of slit 302. For example, and as depicted in FIGS. 3A-3C, in some embodiments the adhesive 202 may be applied only at or near the seal 108. In such embodiments, the leading end 304 and the trailing end 306 may be formed merely by making the slit 302. That is, the leading end 304 and the trailing end 306 may be readily formed as free ends due to the lack of adhesive at or near the slit 302 adhering the label 104 to the outer surface 102 of the bottle 100. Accordingly, the leading end 304 and the trailing end 306 may be easily peeled away from the outer surface 102 of the bottle 100 up until a portion where the label 104 is adhered to the outer surface 102 of the bottle 100 by the adhesive 202. For example, and as depicted in FIG. 3C, the label 104 may be readily peeled away from the outer surface 102 of the bottle 100 up until a portion where the label 104 is adhered to the outer surface 102 of the bottle 100 by the adhesive 202.

Once the slit 302 has been made in the label 104 and the free ends 304 and 306 have been peeled away from circumference of the bottle 100 in the manner described, the only remaining portion of the label 104 still engaging the outer surface 102 of the bottle 100 will be a portion of the label 104 near the seal 108 (adhered to the outer surface 102 via the adhesive 202). For example, and as is illustrated in FIG. 3C, a first portion 202a of adhesive 202 adheres the label 104 to itself at the seal 108 where the first edge 110 overlaps the second edge 112. Further, a second portion 202b of the adhesive 202 adheres a first portion of the label 104 to the outer surface 102 of bottle 100, and a third portion 202c of the adhesive 202 adheres a second portion of the label 104 to the outer surface 102 of the bottle 100.

The adhesive properties of these portions of the adhesive 202 (i.e., the first portion 202a, the second portion 202b, and the third portion 202c) may be tested using the static load label tester 400 as depicted in FIGS. 4 and 5. The static load label tester 400 may be relatively low-cost and easier to use as compared to traditional dynamic testers (e.g., environmental chambers and the like) and may provide test results indicative of how the adhesive 202 will perform in "real world" shipping and storing conditions (e.g., high temperature, relatively humid climates). Thus, the static load label tester 400 may be used to test the adhesive properties of, e.g., the adhesive 202 relatively easily, quickly, and inexpensively, while simulating, e.g., warehouse and other shipping/storing conditions.

Accordingly to one embodiment, the adhesive properties of the adhesive 202 is tested by suspending the bottle 100 in the heated chamber 402 until the adhesive 202 fails, with an elapsed time until failure indicative of the relative adhesive strength of the particular adhesive 202 and/or particular application of the adhesive 202. For example, and as illustrated in FIGS. 4 and 5, the bottle may be suspended in the heated chamber 402 using a support structure 410. In some embodiments, the support structure 410 may include holders 411a and 411b configured to grasp the bottle itself and thus suspend the bottle in the heated chamber 402 as depicted in FIGS. 4 and 5. Although not shown, in other embodiments, rather than the support structure 410 grasping the bottle 100 itself, the leading end 304 of the label 104 may be attached to the support structure 410 using, e.g., a clamp, and the bottle 100 may be suspended in the heated chamber 402 via the label 104. Further, in some embodiments at least a portion of the support structure 410 (including, e.g., the holders 411a and 411b) may be removable from the heated chamber 402 such that, e.g., the portion of support structure 410 may be attached to the bottle 100 and/or the label 104 outside of the static load label tester 400.

In some embodiments, the weighted clamp 412 may be attached to the trailing end 306 of the label 104. The weighted clamp 412 may comprise any suitable means well known in the art for securing the label 104 and/or the trailing end 306. Further, the weighted clamp 412 may comprise a weight 414. The weight 414 may be integrally formed as part of the weighted clamp 412, or may be removably attachable to the weighted clamp 412. In some embodiments, the weight 414 may weigh between 1.0 and 5.0 pounds, and, more preferably, between 1.5 and 2.5 pounds. For example, in some embodiments the weight 414 may weigh approximately 2.0 pounds.

In some embodiments, the static load label tester 400 may further comprise a switch 416 operatively connected to a timing device 418. For example, the timing device 418 may be configured to record an elapsed time until it is stopped via activation of the switch 116, which will be discussed in more detail below.

In operation, a user may remove at least a portion of the support structure 410 from the heated chamber 402 and attach the bottle 100 to the portion of the support structure 410 via, e.g., the holders 411a and 411b. Alternatively, the user may attach the bottle 100 to the support structure 410 inside the heated chamber 402 (e.g., when the support structure 410 is in already in a testing position). The user may also clamp the trailing end 306 into the weighted clamp 412. If the bottle 100 is attached to the support structure 410 outside of the heated chamber 402, the user may then replace the support structure 410 into the heated chamber 402 such that the support structure 410 hangs from, e.g., a ceiling of the heated chamber 402. Accordingly, the bottle 100 will hang below the support structure 410 and the weighted clamp 414 will hang below the bottle 100 via its attachment to the trailing end 306 of the label 104.

Environmental conditions inside the heated chamber 402 may be set by a user using, e.g., an instrument panel 408 to desired test conditions. In some embodiments, an internal temperature of heated chamber may be set to a temperature higher than an ambient temperature outside of the static load label tester 400. For example, an internal temperature of the heated chamber 402 may be set at 90 to 110 degrees Fahrenheit. In some embodiments, an internal temperature of the heated chamber 402 may be set at approximately 100 degrees Fahrenheit.

Any other desired testing condition may also be set at the instrument panel 408 and/or regulated inside the heated chamber 402 by the static load label tester 400. For example, in some embodiments the relative humidity inside the heated chamber 402 may be maintained at, e.g., 75% humidity to 95% humidity. In some embodiments, the relative humidity inside heated chamber may be maintained at approximately 85% humidity. Further, in some embodiments, the bottle 100 may be filled with a liquid before placing it in the testing position depicted in FIGS. 4 and 5. For example, in some embodiments the bottle 100 may be filled with water. In some embodiments, the bottle 100 may be filled with a warmed liquid, such as warm water.

In this testing position (i.e., the position depicted in FIGS. 4 and 5) the adhesive 202 is subject to shear forces (due to, e.g., the weighted clamp 412 and any weight 414 attached thereto, the weight of the bottle 100 and any liquid within, expansion of the bottle 100 in the vicinity of the adhesive 202, etc.) as well as the regulated testing conditions (e.g., increased temperature, humidity). Further, in some embodiments, the adhesive 202 may experience further heating due to, e.g., a warm liquid provided within the bottle 100 as discussed. Thus, while in the testing position, the adhesive 202 may experience conditions and/or forces simulating those normally experienced during storing and/or shipping of the bottle 100. For example, during shipping and/or storing, the bottle 100 may typically be stored in a warehouse with elevated temperatures and/or humidity. Due to these environmental conditions, a consumable liquid contained within the bottle 100 and/or the bottle 100 itself may expand, causing increased shear forces acting on the bond between the adhesive 202 with the label 104 and/or the outer surface 102 of bottle 100.

Eventually, the shear forces acting on the adhesive 202 as well as the testing conditions within the heated chamber 402 may cause the adhesive 202 to fail. For example, the shear forces acting on the adhesive 202 may cause the first portion 202a of the adhesive 202 at seal 108 to fail, or may cause the second portion 202b or the third portion 202c between the label 104 and the outer surface 102 of the bottle 100 to fail. In such failure, the weighted clamp 412 may fall (as either the label 104 becomes disengaged from itself and/or the label 104 becomes disengaged from the outer surface 102 of the bottle 100). A user may thus measure an elapsed time from when the bottle 100 first is allowed to hang below support clamp 410 until the adhesive 202 fails (e.g., when weighted clamp 412 falls) as an indication of the relative strength of that particular adhesive 202 and/or application of the adhesive 202. For example, applications which take longer to fail may be considered a relatively stronger bond than applications that take shorter to fail.

In embodiments of the static load label tester 400 which comprise the switch 416 and the timing device 418, at least a portion of the timing to failure can be automated. For example, the switch 416 may be operatively connected to the timing device 418 such that the switch 416 stops the timing device 418 when a force is applied to the switch 416. In such embodiments, the user may start the timing device 418 when the bottle is suspended in the heated chamber 402, such that the timing device 418 begins to record an elapsed time to failure of the adhesive 202. When the adhesive 202 ultimately fails, the weighted clamp 412 and/or the weight 414 will fall onto the switch 416, applying a force to the switch 416. This force will thus cause the switch 416 to stop the timing device 418, such that the timing device 418 no longer records an elapsed time. Accordingly, for such embodiments the static load label tester 400 may be configured to automate at least a portion of the timing until failure of the adhesive 202.

Figure 6:
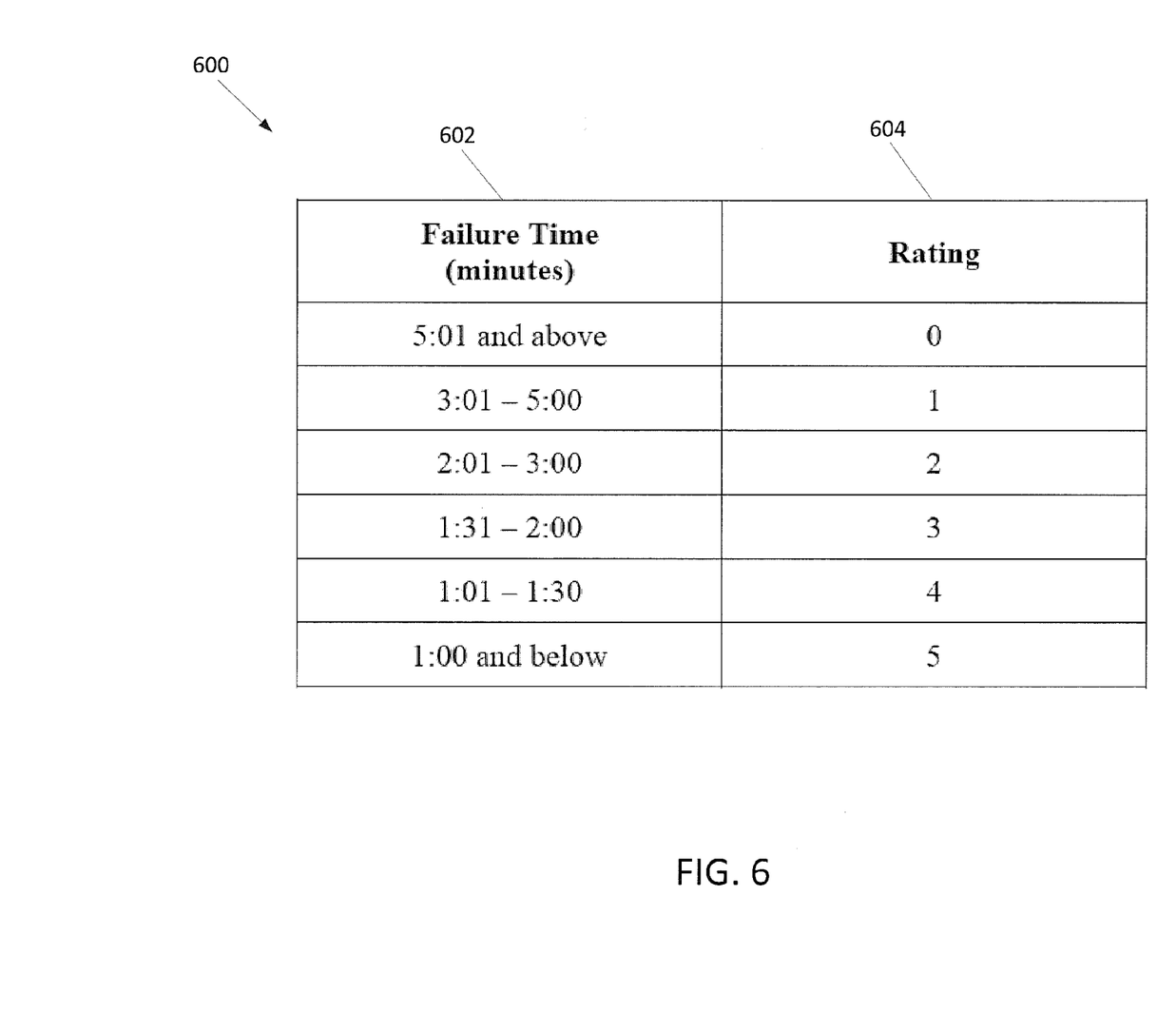
FIG. 6 is an example table correlating elapsed failure times of an adhesive of the bottle depicted in FIG. 1 with a corresponding numerical rating according to some aspects of the disclosure.

In some embodiments, an elapsed time may be converted to a metric in order to compare the relative adhesiveness of that particular application with other applications and/or predetermined benchmarks. For example, as depicted in FIG. 6, an adhesive rating table 600 may be used to further quantify an adhesiveness of a particular application and compare it to, e.g., other batches, benchmark applications, etc. For example, a numerical rating, as listed in a rating column 604, may be assigned to the bottle 100 according to a measured failure time as indicated in a failure time column 602. In this embodiment, the lower the rating, the more effective the application of the adhesive 202. Thus, a bottle 100 where the adhesive 202 failed in the static load label tester 400 in 5 minutes and 35 seconds may receive a rating of 0, while a bottle 100 whose adhesive 202 failed in 1 minute and 46 seconds may receive a rating of 3. Thus, the application of the adhesive 202 in the first batch (which received a rating of 0) may quickly be determined to be superior to the application of the adhesive 202 in the second batch (which received a rating of 3).

In some embodiments, a user may require a particular batch of bottles 100 to receive a minimum benchmark rating in order to be determined to "pass" and thus be acceptable for shipping. For example, in some embodiments a batch of bottles 100 must receive a 0, 1, or 2 rating to be acceptable (pass). Bottles 100 with a rating of 3 or higher may be considered to fail (e.g., a rating of 3 or higher is indicative that the labels 104 will become loose and/or be inadvertently removed during shipping/storing of the bottles 100). Thus, a bottler or the like may immediately test a batch of bottles 100 after applying an adhesive 202 to determine a proper rating of the bottle 100 and whether or not such rating conforms to "passing" standards. Returning to the previous example, the bottles 100 in the first batch (whose adhesive 202 failed after 5 minutes and 35 seconds) may be rated a "0" and thus pass (e.g., the bottles 100 may be shipped for distribution). However, the bottles 100 in the second batch (whose adhesive 202 failed after 1 minute and 46 seconds) may be rated a "3" and thus fail (e.g., the bottles 100 may be re-labeled or destroyed). Those skilled in the art, given the benefit of this disclosure, will appreciate that the values contained in the failure time column 602 and the rating column 604 of the adhesive rating table 600 are merely illustrative and, in practice, the elapsed time and/or ratings may vary without departing from the scope of this disclosure.

Figure 7:
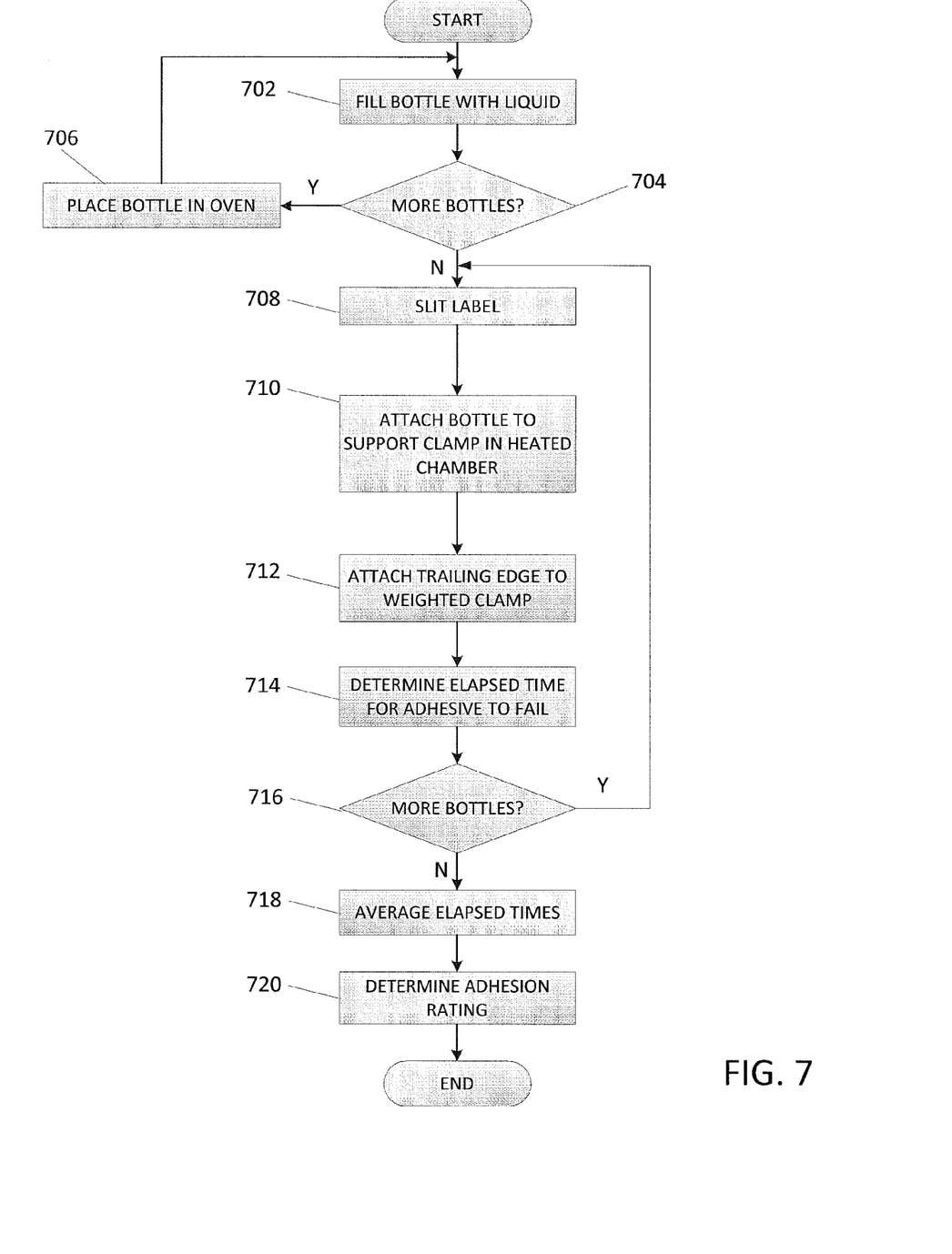
FIG. 7 is a flowchart of a method for assessing the adhesion of a label to an outside surface of a bottle according to some aspects of the disclosure.

FIG. 7 depicts an illustrative flowchart for a method of assessing the label 104 adhesion to one or more bottles 100 according to some aspects of the disclosure. At step 702, a user fills a bottle 100 with a liquid. As discussed, in some embodiments, the user may fill the bottle 100 with warm water. In some embodiments, a user may wish to test a plurality of bottles 100, such as multiple bottles 100 labeled during a common labeling batch or the like. At step 704, if more bottles 100 are to be tested, the method proceeds to step 706 where the user may place the bottle 100 in an oven. Placing each bottle 100 in an oven may keep the temperature of the liquid within the bottle 100 elevated until the bottle 100 is ultimately tested. Once there are no more bottles 100 to be filled with warm liquid, the method proceeds to step 708. At step 708, the user slits the label 104 of a first bottle 100 to be tested in a manner as described, forming a leading end 304 and a trailing end 306. For example, in some embodiments the user may slit the label 104 in a generally vertical orientation at a location approximately 180 degrees around the circumference of the bottle 100 from a seal 108 in the label 104 on the bottle 100. The user then attaches the bottle to the support structure 410 within the heated chamber 402 at step 710, and, in some embodiments, a trailing end 306 of the label 104 to a weighted clamp 412 (with or without the weight 414) at step 712. Although not depicted in the flowchart in FIG. 7, in alternative embodiments the user may attach the leading end 304 of the label 104 to the support structure 410 instead of or in addition to attaching the bottle 100 to the support structure 410, and/or may attach the bottle 100 and/or the leading end 304 of the label 104 to the support structure 410 outside of the static load label tester 400.

As discussed, the bottle 100 is suspended in the heated chamber 402 such that the support structure 410 engages, e.g., a ceiling of the heated chamber 402, with the bottle 100 hanging below the support structure 410, and the weighted clamp 412 hanging below the bottle 100 via its attachment to the trailing end 306 of the label 104. At step 714, the user may determine an elapsed time for the adhesive 202 to fail. As discussed, this may occur when either the bond between two portions of the label 104 fails and/or the bond between the label 104 and the outer surface 102 of the bottle 100 fails such that the weighted clamp 412 falls. In embodiments comprising the switch 416 operatively connected to the timing device 418, at least a portion of step 714 may be automated as discussed. For example, the timing device 418 may be configured to stop recording the elapsed time when the weighted clamp 412 (with or without the weight 414) falls and applies a force to the switch 416. At step 716, if there are more bottles 100 to be tested (e.g., if the user is testing multiple bottles 100 from a single batch, etc.), then the method returns to step 708 at which point the user removes the next bottle 100 from an oven and continues through each step 708-714 as described above.

Once each bottle 100 has been tested (e.g., once an elapsed time to failure has been determined for each bottle 100 to be measured), the elapsed times to failure for each bottle 100 in the tested batch is averaged at step 718. Finally, at step 720, the averaged time to failure may be converted to a metric and/or compared to a benchmark or the like (as discussed in connection with FIG. 6) to determine if the tested adhesion is suitable for shipping, etc. (e.g., if the tested adhesion is likely to withstand environmental conditions faced during shipping/storing the bottles 100).

While the invention has been described with respect to certain preferred embodiments, as will be appreciated by those skilled in the art, it is to be understood that the invention is capable of numerous changes, modifications, and rearrangements and such changes, modifications, and rearrangements are intended to be covered by the following claims.

What is claimed is:

1. A method for testing adhesion of a label to a bottle, the method comprising:
  filling a bottle comprising a label adhered to an outside surface of the bottle with liquid that has a temperature greater than the temperature of the bottle;
  slitting the label adhered to the outside surface of the bottle to form a leading end and a trailing end of the label at the slit;
  attaching the bottle to a support structure within a heated chamber;
  suspending a weight from the trailing edge such that it hangs below the support structure; and
  determining an elapsed time before the label disengages from the bottle.

2. The method of claim 1 further comprising placing the bottle in an oven prior to the attaching the bottle to the support structure.

3. The method of claim 1, wherein the weight weighs between 1.0 pounds and 5.0 pounds.

4. The method of claim 1, wherein the label comprises a seal where a first portion of the label is adhered to a second portion of the label, and wherein slitting the label comprises slitting the label at a position located 180 degrees around the bottle from the seal.

5. The method of claim 4, wherein the seal comprises a first edge of the label overlapping a second edge of the label, wherein the first edge and the second edge are substantially parallel, and wherein slitting the label further comprises slitting the label in a direction substantially parallel to the first edge of the label and the second edge of the label.

6. The method of claim 1, wherein the heated chamber is configured to heat air within the heated chamber to a temperature in a range of 90 degrees Fahrenheit to 110 degrees Fahrenheit.

7. The method of claim 1, further comprising translating the elapsed time to a numerical rating.

8. A method for testing adhesion of labels to bottles, the method comprising:
  filling a plurality of bottles, each comprising a label adhered to an outside surface of the bottle, with liquid that has a temperature greater than the temperature of the bottle;
  for each of the plurality of bottles:
  slitting the label adhered to the outside surface of the bottle to form a leading end and a trailing end of the label at the slit;
  attaching the bottle to a support structure;
  suspending the bottle in a heated chamber via the support structure such that the bottle hangs below the support structure; and
  determining an elapsed time before the label disengages from the bottle; and
  averaging the elapsed time for each bottle to form an average elapsed time for the plurality of bottles.

9. The method of claim 8 further comprising:
  placing the plurality of bottles in an oven; and
  for each of the plurality of bottles, removing the bottle from the oven prior to slitting the label.

10. The method of claim 8 further comprising, for each of the plurality of bottles, fixing a weight to the trailing end of the label, wherein when the bottle is suspended in the heated chamber, the weight hangs below the bottle.

11. The method of claim 10, wherein the weight weighs between 1.0 pounds and 5.0 pounds.

12. The method of claim 8, wherein the label on each of the plurality of bottles comprises a seal where a first portion of the label is adhered to a second portion of the label, and wherein slitting the label comprises, for each of the plurality of bottles, slitting the label at a position located 180 degrees around the bottle from the seal.

13. The method of claim 12, wherein the seal on each of the plurality of bottles comprises a first edge of the label overlapping a second edge of the label, wherein the first edge and the second edge are substantially parallel, and wherein slitting the label further comprises, for each of plurality of bottles, slitting the label in a direction substantially parallel to the first edge of the label and the second edge of the label.

14. The method of claim 8, wherein the heated chamber is configured to heat air within the heated chamber to a temperature between of 90 degrees Fahrenheit and 110 degrees Fahrenheit.

15. The method of claim 8, further comprising translating the average elapsed time to a numerical rating.

16. An apparatus for testing the adhesion of a label to a bottle, the apparatus comprising:
  a weighted clamp configured to attach to a trailing end of a label adhered to an outside surface of a bottle filled with a liquid that has a temperature greater than the temperature of the bottle, wherein the trailing end of the label is a first end of the label formed along a slit of the label;
  a support structure configured to attach to the bottle; and
  a heated chamber configured to receive the weighted clamp and the support structure in a testing position, wherein, when in the testing position, the weighted clamp hangs below the support structure.

17. The apparatus of claim 16, wherein the support structure is configured to move between the testing position and a removed position, wherein, when in the removed position, the support structure is outside of the heated chamber.

18. The apparatus of claim 16 further comprising a switch operatively connected to a timing device, wherein the switch is configured to stop the timing device when the switch is engaged by the weighted clamp.

19. The apparatus of claim 16, wherein the weighted clamp weighs between 1.0 pounds and 5.0 pounds.

20. The apparatus of claim 16, wherein the heated chamber is further configured to heat air within the heated chamber to a temperature in a range of 90 degrees Fahrenheit to 110 degrees Fahrenheit.

* * * * *